(12) United States Patent
Corma Canos et al.

(10) Patent No.: US 8,426,633 B2
(45) Date of Patent: Apr. 23, 2013

(54) CARBONYLATION PROCESS FOR THE PRODUCTION OF ACETIC ACID AND/OR METHYL ACETATE

(75) Inventors: Avelino Corma Canos, Valencia (ES); Gordon John Haining, East Riding of Yorkshire (GB); David John Law, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 225 days.

(21) Appl. No.: 12/735,180

(22) PCT Filed: Dec. 16, 2008

(86) PCT No.: PCT/GB2008/004136
§ 371 (c)(1),
(2), (4) Date: Jun. 18, 2010

(87) PCT Pub. No.: WO2009/081099
PCT Pub. Date: Jul. 2, 2009

(65) Prior Publication Data
US 2010/0267985 A1    Oct. 21, 2010

(30) Foreign Application Priority Data
Dec. 20, 2007    (EP) .................................... 07254975

(51) Int. Cl.
*C07C 67/36*    (2006.01)
*C07C 51/12*    (2006.01)

(52) U.S. Cl.
USPC .......................................... 560/232; 562/519

(58) Field of Classification Search .......................... None
See application file for complete search history.

(56) References Cited

U.S. PATENT DOCUMENTS

| | | | | |
|---|---|---|---|---|
| 3,760,062 | A * | 9/1973 | Sand et al. | 423/700 |
| 4,205,052 | A * | 5/1980 | Rollmann et al. | 423/706 |
| 4,564,512 | A | 1/1986 | Baacke et al. | |
| 4,612,387 | A * | 9/1986 | Feitler | 560/232 |
| 6,387,842 | B1 | 5/2002 | Wegman | |
| 2006/0287551 | A1* | 12/2006 | Cheung et al. | 560/232 |
| 2007/0238897 | A1* | 10/2007 | Cheung et al. | 560/232 |

FOREIGN PATENT DOCUMENTS
WO    2005/105720    11/2005
WO    2006/121778    11/2006

OTHER PUBLICATIONS

International Search Report for PCT/GB2008/004136, mailed Feb. 19, 2009.
Written Opinion of the International Searching Authority for PCT/GB2008/004136, mailed Feb. 19, 2009.

* cited by examiner

*Primary Examiner* — Karl J Puttlitz
(74) *Attorney, Agent, or Firm* — Nixon & Vanderhye

(57) ABSTRACT

Process for the manufacture of at least one of acetic acid and methyl acetate by carbonylating at least one carbonylatable reactant selected from methanol, dimethyl ether and dimethyl carbonate with carbon monoxide in the presence of a zeolite of structure type MOR. The zeolite has greater than 50% of its crystals in the size range to 3 microns.

13 Claims, 6 Drawing Sheets

CARBONYLATION PROCESS FOR THE PRODUCTION OF ACETIC ACID AND/OR METHYL ACETATE

This application is the U.S. national phase of International Application No. PCT/GB2008/004136, filed 16 Dec. 2008, which designated the U.S. and claims priority to European Application No. 07254975.1, filed 20 Dec. 2007, the entire contents of each of which are hereby incorporated by reference.

This invention relates to a process for the production of acetic acid and/or methyl acetate by the carbonylation of at least one of dimethyl ether, dimethyl carbonate and methanol in the presence of a zeolite catalyst of the MOR structure type.

BACKGROUND OF THE INVENTION

The zeolite mordenite is known to be suitable for use as a catalyst for the carbonylation of feedstocks such as methanol, dimethyl ether and dimethyl carbonate to produce the carbonylation products methyl acetate and/or acetic acid.

EP-A-0 596 632 describes a vapour phase process for the carbonylation of methanol to produce acetic acid in the presence of a modified mordenite catalyst at high temperatures and pressures.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of a modified mordenite catalyst at a temperature in the range 250 to 600° C. and at a pressure in the range 10 to 200 bar.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst.

Without wishing to be bound by theory, it is believed that the sorption or catalytic transformation of the reactants to products by zeolites such as mordenite is effected within the channels of the zeolite crystals.

U.S. Pat. No. 4,205,052 describes a process for manufacturing synthetic mordenite in which the shape or size of the mordenite crystals is controlled by including an organic basic nitrogen compound in the forming solution. The process was used to prepare crystals in the size range of 0.5 to 20 microns.

U.S. Pat. No. 4,564,512 describes a process for the production of coarse particle mordenite of size 20 microns to 300 microns by treating a reaction mixture produced from aqueous sodium aluminate, silica, sodium chloride solution and water at a temperature of 140° to 180° C. until formation of crystals, separating the crystalline product, washing with water and drying.

SUMMARY OF THE INVENTION

Generally, in industrial chemical processes in which catalysts are used, attempts are made to improve the performance of a catalyst. It is desirable to improve catalytic activity and/or selectivity to the desired products and/or improve catalyst lifetime. It has now been found that in carbonylation processes such as the carbonylation of methanol, dimethyl ether or dimethyl carbonate in the presence of a zeolite of structure type MOR, improved catalytic performance can be achieved by using an MOR zeolite which has small crystals and/or small particles.

Accordingly, the present invention provides a process for the manufacture of at least one of acetic acid and methyl acetate by the carbonylation of at least one carbonylatable reactant selected from methanol, dimethyl ether and dimethyl carbonate with carbon monoxide in the presence of a zeolite catalyst of structure type MOR and wherein the zeolite has a crystal size of no greater than 3 microns.

The term 'structure type MOR' as used in the context of the present invention denotes the IUPAC Commission of Zeolite Nomenclature. Zeolite materials of structure type MOR are well known and defined in, for example, the *Atlas of Zeolite Framework Types* (C. Baerlocher, W. M. Meier, D. H. Olson, 5$^{th}$ ed. Elsevier, Amsterdam, 2001). In addition, a web-based version of the database of zeolite structures may be found at (http://www.iza-structure.org/databases/) and is a compendium of topological and structural details about zeolite structure types (frameworks), including the types of ring structures present in a zeolite and the dimensions of the channels defined by each ring type.

Zeolites of structure type MOR are characterised by having an 8-member ring channel which is interconnected with a channel defined by a ring with 12 members. The 8-membered ring has a window size of 2.6 Angstroms by 5.7 Angstroms. The 12-membered ring has a window size of 6.5 Angstroms by 7.0 Angstroms.

Zeolites with structure type MOR are exemplified by mordenite. The structure of mordenite is well known and is defined, for example in the afore-mentioned database of zeolite structures. Mordenite in the hydrogen form has elliptical 6.5×7.0 Angstrom channels (12 member rings with window openings running in the crystallographical c-direction). It also has a system of smaller channels running perpendicular to the 12 member ring channels (and running in the b-direction). These small channels consist of 3.4×4.8 Angstrom channels having 8 member ring windows of these dimensions. The mordenite structure also possesses a zig-zag Y-branching of the pore structure due to twisted 8 member rings (in the crystallographic c-direction) This results in a distorted window to each side of the Y-branching of 2.6×5.7 Angstroms.

Preferably, the MOR zeolite for use in the process of the present invention has a $MO_2:X_2O_3$ molar ratio of at least 5, wherein X is selected from aluminium, boron, iron, gallium and mixtures thereof and M is selected from at least one of silicon, germanium and tin. Generally, X will be aluminium except where framework aluminium atoms have been replaced by one or more of boron, iron and gallium. Generally, M will be silicon except where framework silicon atoms have been replaced by one or more of germanium and tin. Typically, the MOR zeolite will have a silica:alumina molar ratio in the range 6 to 90:1 such as 10 to 40:1.

The crystal size of the MOR zeolite has been found to be an important factor affecting the catalytic performance of the MOR zeolite in a carbonylation process. By the term 'crystal size' is meant the size of a discrete crystal. The crystal size of the MOR zeolite employed in the carbonylation process is in the range greater than 0 to 3 microns, preferably in the range 0.1 to 3 microns, more preferably, in the range 0.1 to 2.5 microns, especially in the range 0.1 to 2 microns, such as 0.1 to 1.5 microns. Preferably, the MOR zeolite has a predominant amount (>50%) of crystals which are in the size range greater than 0 to 3 microns, preferably in the range 0.1 to 3 microns, more preferably, in the range 0.1 to 2.5 microns, especially in the range 0.1 to 2 microns, such as 0.1 to 1.5 microns. Suitably, greater than 80% of the crystals are in the size range greater than 0 to 3 microns, preferably in the range 0.1 to about 3 microns, more preferably, in the range 0.1 to 2.5 microns, especially in the range 0.1 to 2 microns, such as 0.1 to 1.5 microns.

Crystal size can be determined using conventional techniques such as high resolution scanning electron microscopy (SEM) and transmission electron microscopy (TEM). Such techniques are capable of having a resolution below 0.1 microns.

In addition to crystal size, it has also been found that the particle size of the MOR zeolite is a factor associated with catalytic performance in a carbonylation process. It has been found that the effect on catalytic performance is more pronounced when the MOR zeolite has an average particle size of no greater than 6 microns. The average particle size of the MOR zeolite employed in the carbonylation process is no greater than 6 microns, preferably in the range 2 to 6 microns, such as in the range 2 to 3.5 microns. It has been found that particles of size no greater than 6 microns provide improved activity and selectivity to the desired carbonylation products compared to the use of larger size particles.

The term 'average particle size' as used herein, means the arithmetic mean particle size, d50. d50 is a standard parameter used in particle size analysis and is defined as: $-d50=\Sigma n_i d_i/\Sigma n_i$ where n is the number of particles with a measured diameter d and i is the increment in the data is collected, usually 0.5 or 1.0 micron intervals. The definition and description of the parameter d50 can be found in the Characterisation of Heterogeneous Catalysts. Ed. Francis Delanney published by Marcel Dekker Inc., 1984, p 305-308.

The parameter d50 may be measured using commercially available laser light diffraction particle size analysers, such as those manufactured by Malvern Instruments.

In a preferred embodiment of this invention, the MOR zeolite has a predominant amount (>50%) of crystals having a size in the range 0.1 to 2 microns and an average particle size in the range greater than 0 to 6 microns, more preferably, a crystal size in the range 0.1 to 2 microns and an average particle size in the range 2 to 6 microns, especially a crystal size in the range 0.1 to 1.5 microns and an average particle size in the range 2 to 3.5 microns.

In a more preferred embodiment of this invention, the MOR zeolite is a mordenite and the mordenite has a predominant amount (>80%) of crystals having a size in the range in the range 0.1 to 2 microns and an average particle size in the range greater than 0 to 6 microns, more preferably a crystal size in the range 0.1 to 2 microns and an average particle size in the range 2 to 6 microns, especially a crystal size in the range 0.1 to 1.5 microns and an average particle size in the range 2 to 3.5 microns.

Zeolites of structure type MOR having a variety of crystal and particle sizes suitable for use in the carbonylation process of the present invention are available from a variety of commercial sources, such as Zeolyst International, Zeochem AG and Süd-Chemie AG. The zeolite, mordenite is commercially available in the Na, $NH_4$ form or H-form. The $NH_4$ form can be converted to the acid (H-form) by known techniques, such as by calcining at high temperature. The Na form can be converted to the acid (H-form) by converting first to an $NH_4$ form by ion exchange with ammonium salts such as ammonium nitrate. Alternatively, MOR zeolites may be synthesised using known techniques. The preparation of mordenite from aqueous inorganic compositions is well known and there are recipes in the literature for making synthetic mordenite having small crystals. For example the method described in U.S. Pat. No. 4,205,052 can be used to prepare crystals of 3 microns or less.

Depending upon the precise synthesis method used, the MOR zeolite produced may contain alkali metals such as sodium and potassium and/or alkaline earth metals such as calcium. For use in a carbonylation process, it is preferred that the level of such alkali and alkaline earth metal contaminants is kept below a total of 10,000 ppm.

The MOR zeolite preferably has a surface area as measured by nitrogen BET of greater than 100 $m^2/g$, more preferably greater than 300 $m^2/g$.

For use in a carbonylation process to produce methyl acetate and/or acetic acid, the MOR zeolite is preferably employed in the acid form (H-form) or in a metal loaded form wherein the zeolite has been ion-exchanged or otherwise loaded with one or more metals such as copper, silver, gold, nickel, iridium, rhodium, platinum, palladium or cobalt.

The metal loading on the MOR zeolite may be expressed in terms of the fractional loading of the metal as gram atoms of metal per gram atom of aluminium in the zeolite. The metal loading can also be expressed as a mole percentage loading relative to aluminium in the MOR zeolite through the relationship:

$$\text{mol \% Metal}=(\text{gram atoms Metal/gram atoms aluminium})\times 100$$

Thus, for example, a loading of 0.55 gram atoms of copper per aluminium in the MOR zeolite equates to a 55 mol % loading of copper relative to aluminium in the zeolite.

Suitably, the metal loading may be in the range of 1 to 200 mol % relative to aluminium, for example, 5 to 120 mol %, such as 5 to 110 mol %.

The MOR zeolite framework, may in addition to the silicon and aluminium atoms, contain additional trivalent elements, such as boron, gallium and/or iron.

Where the MOR zeolite contains at least one or more trivalent framework, the metal loading in the zeolite can be expressed in terms of the fractional loading of the metal as gram atoms of metal per gram atom of total trivalent elements in the zeolite. The metal loading can also be expressed as a mole percentage loading relative to total trivalent elements in the zeolite through the relationship:

$$\text{mol \% Metal}=(\text{gram atoms Metal/gram atoms of total trivalent elements})\times 100.$$

The MOR zeolite framework, may in addition to the silicon and aluminium atoms, contain additional tetravalent elements, such as germanium and tin.

If the carbonylation reaction is to be conducted substantially in the absence of water, it is preferred that the MOR zeolite is dried prior to use. The zeolite may be dried, for example by heating to a temperature of 400 to 500° C.

Suitably, the MOR zeolite is activated immediately before use in the carbonylation reaction by heating the zeolite at elevated temperature for at least one hour under flowing nitrogen, carbon monoxide, hydrogen or mixtures thereof.

Where dimethyl ether or dimethyl carbonate is used as the carbonylatable reactant, the carbonylation process is typically carried by passing dimethyl ether or dimethyl carbonate, carbon monoxide and, if desired hydrogen, through a fixed or fluidised bed of MOR zeolite catalyst, such as mordenite, maintained at the required temperature, such as in the range 150 to 350° C., such as in the range 250 to 350° C. The process is typically carried out under substantially anhydrous conditions, that is, using less than 2.5 wt % water in the gaseous feed and at a total reaction pressure in the range 1 to 100 bar and a gas hourly space velocity in the range 500 to 40,000 $h^{-1}$.

Where the carbonylatable reactant is dimethyl ether or dimethyl carbonate the primary product of the carbonylation reaction is methyl acetate but some acetic acid may also be formed.

Where methanol is used as the carbonylatable reactant, the carbonylation process is typically carried by passing the methanol, carbon monoxide and, if desired, hydrogen through a fixed or fluidised bed of MOR zeolite catalyst, such as mordenite, maintained at the required temperature, such as in the range 250 to 400° C., such as 275 to 350° C. The process is typically carried out at a total reaction pressure in the range 1 to 100 bar.

Where the carbonylatable reactant is methanol the dominant product of the carbonylation reaction will be acetic acid, but some methyl acetate may be present, depending on the degree of conversion of methanol.

The carbon monoxide employed in the carbonylation process may be substantially pure carbon monoxide, for example, carbon monoxide typically provided by suppliers of industrial gases, or it may contain impurities that do not interfere with the conversion of methanol to acetic acid or dimethyl ether or dimethyl carbonate to methyl acetate, such as nitrogen, helium, argon, methane and/or carbon dioxide.

The carbonylation process may be conducted in the presence of hydrogen, thus the carbon monoxide feed may contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide. The molar ratio of carbon monoxide:hydrogen may be in the range 1:3 to 15:1. The molar ratio of carbon monoxide to dimethyl ether or dimethyl carbonate may be in the range 1:1 to 99:1. The molar ratio of carbon monoxide to methanol is suitably in the range 1:1 to 60:1.

The carbonylation process may be carried out as a batch or a continuous process, preferably as a continuous process.

BRIEF DESCRIPTION OF THE DRAWINGS

The invention is further described with reference to the accompanying drawings, in which.

Figure 1:
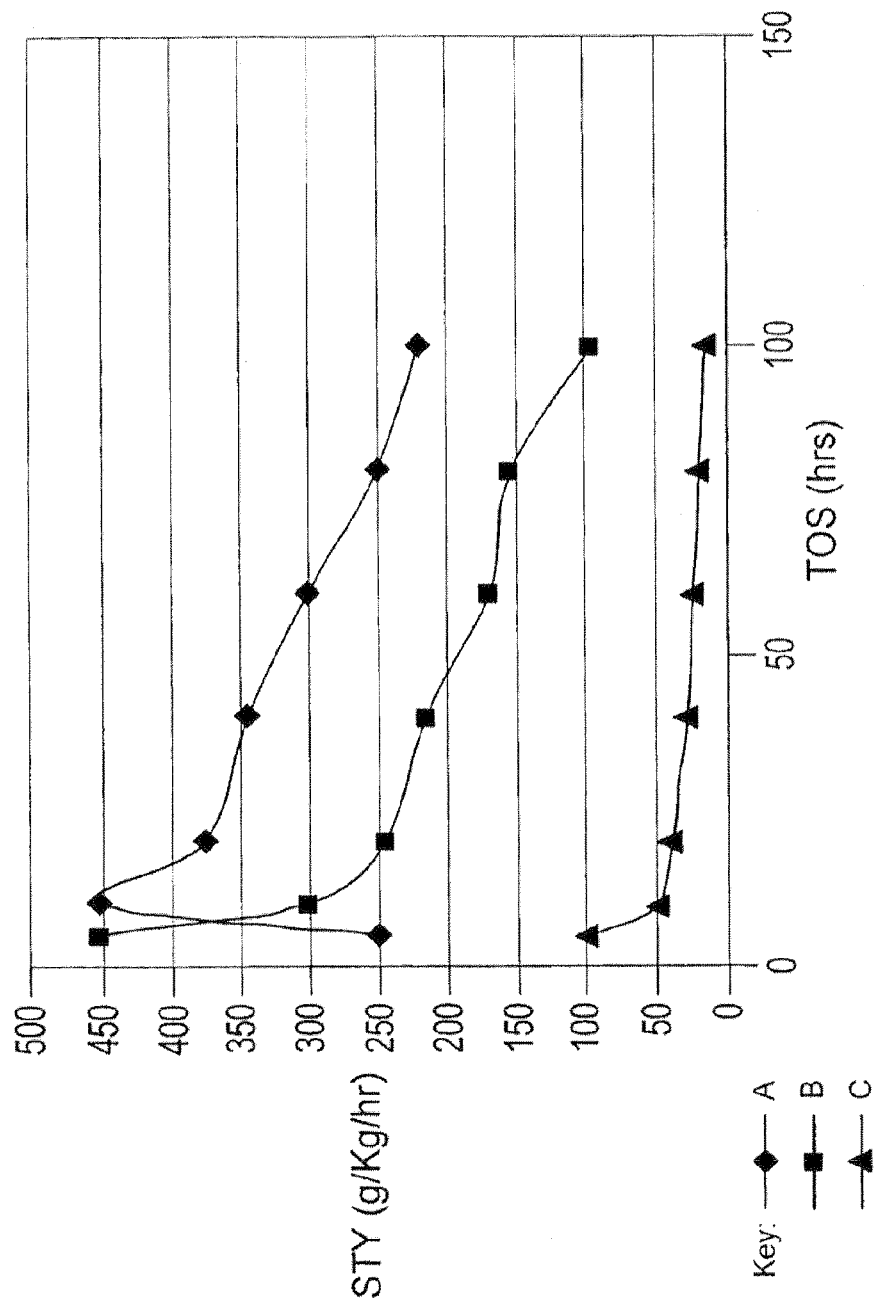
FIG. 1 depicts STY to acetyls products (g kg$^{-1}$ h$^{-1}$) versus time on stream (hours) for the carbonylation of dimethyl ether using mordenite catalysts of varying average particle sizes.

The invention is now illustrated with reference to the following Examples.

EXAMPLE 1 d50 Particle Size Determination

The average particle size, d50, of each of three commercially available mordenites (in the ammonium form), designated A to C was determined using a Mastersizer 2000 laser light diffraction particle size analyser (Malvern Instruments). At least 50% of the crystals of each mordenite were in the range 0.1 to 1.5 microns. A slurry of each mordenite was prepared by adding 20 mls of deionised water and 0.1 g of sodium hexametaphosphate to approx. 1 g of a mordenite. Sufficient slurry was added to approximately 800 mls of water such that the blue obscuration bar was between 12 and 20%. The slurry in water was then analysed to determine the average particle size of a mordenite. The results are given in Table 1.

TABLE 1

| Mordenite | Silica:alumina ratio | Particle Size, d50 (microns) |
| --- | --- | --- |
| A | 20 | 2.3 |
| B | 20 | 2.75 |
| C | 18 | 11.7 |

Calcination of Mordenites A, B and C

Prior to preparing copper loaded mordenites from the mordenites A, B and C, each of the mordenites was converted from its ammonium form to the hydrogen form (H-form) by calcination. The calcination was carried out by heating each mordenite at 90° C. for 2 hours, then at 110° C. for 2 hours and then at 500° C. for 3 hours. The H-mordenite so produced was then cooled in air, pressed with a hydraulic press (12 tons), ground with a mortar and pestle and sieved to pellets of size fraction of 250 to 500 microns.

Preparation of Copper Mordenite Catalysts A, B and C 80 g of a H-mordenite was weighed into a 500 ml round bottomed flask together with 14.29 g of copper (II) nitrate hemipentahydrate (98% ACS) and a stirrer bar. Sufficient deionised water (ca. 100 mL) was added to the flask to obtain a thick slurry. The top of the flask was covered loosely and stirred overnight. The copper mordenite was then dried under reduced vacuum using a rotary evaporator before being dried in an oven at 90° C. for 12 hours. The copper mordenite was then calcined in a muffle oven (oven volume=18 L) under a static atmosphere of air using the following temperature programme. The temperature was increased from room temperature to 90° C. at a ramp rate of 3° C./min and held at this temperature for 2 hours. The temperature was then increased from 90° C. to 110° C. at a ramp rate of 1° C./min and held at this temperature for 2 hours. The temperature was then increased from 110° C. to 500° C. with a ramp rate of 5° C./min and held at this temperature for 6 hours before cooling to room temperature. The copper mordenite was compacted at 12 tonnes in a 33 mm die set using a Specac Press, and crushed and sieved to pellets of size fraction of 250 to 500 microns. The mordenite had a copper loading of ca. 55 mole % of the amount of aluminium contained in the mordenite. Copper mordenites prepared from the mordenites A, B and C are referred to as catalyst A, B and C respectively.

Carbonylation of Dimethyl Ether

Each of catalysts A, B and C was used to catalyse the carbonylation of dimethyl ether as follows. A stainless steel reactor tube containing 2.0 ml catalyst topped with 1 ml glass beads was mounted in the downstream leg of a stainless steel U-tube. The upstream leg of the U-tube was packed with glass beads. The catalyst was heated from ambient temperature to 100° C. at a ramp rate of 3° C./min under helium gas at a pressure of 46.7 barg and a flow rate of 125 ml/min NTP (20° C. and 1 atm) for 18 hours. The catalyst was then heated from 100° C. to 300° C. at a ramp rate of 3° C./min under a gas feed of 48.4 vol % carbon monoxide, 48.4 vol % hydrogen and 3.2 vol % helium at a pressure of 46.7 barg and a flow rate of 202 ml/min NTP (20° C., 1 atm) for 2 hours. Liquid dimethyl ether (BOC, >99.99%) was then fed to the reactor at a rate of 0.0185 mL/min from a high pressure syringe pump (syringe barrel at 5° C.) onto the glass beads in the upstream leg of the U-tube where it vaporised and mixed with the gas feed before passing over the catalyst. The reactor pressure was controlled by a pressure control valve downstream of the reactor and the temperature of the reactor effluent gas was maintained at at least 150° C. The reactor effluent gas was let down to atmospheric pressure across the pressure control valve. The effluent gas was cooled to 60° C. and passed through a knock-out pot to trap involatile materials before the effluent stream was passed to a mass spectrometer and gas chromatograph for acetyls product analysis. The space time yield (STY) of acetyls products was calculated as the molar equivalent weight of acetic acid corresponding to the sum of the methyl acetate and acetic acid produced expressed as grams of acetic acid per hour per kilogramme of catalyst. The results of the carbonylation reactions are given in FIG. 1.

From FIG. 1 it can be seen that catalysts A and B having smaller mordenite particle sizes than catalyst C, demonstrate superior catalytic activity to that of catalyst C.

EXAMPLE 2

Carbonylation of Dimethyl Carbonate Using H-Mordenite Catalysts D, E and F

Properties of three commercially available mordenites in the ammonium form are given in Table 2 below. The mordenites have been designated, mordenites D, E and F.

TABLE 2

| Mordenite | Na (ppm) | K (ppm) | Ca (ppm) | Silica:alumina ratio | Crystal size (microns) | Particle size d50 (microns) |
|---|---|---|---|---|---|---|
| D | <1000 | <500 | <500 | 20 | 0.5-1.5 | 2.3 |
| E | <500 | <500 | <50 | 15 | 1 | 3.1 |
| F | <500 | <500 | <50 | 14 | 1-2 | 9.8 |

The average particle size, d50 of the mordenites D, E and F was determined using a Mastersizer 2000 laser light diffraction particle size analyser (Malvern Instruments) using the method as described in Example 1 above.

The crystal size of >80% of the crystals was determined by scanning electron microscopy (SEM).

Calcination of Mordenites D, E and F

Prior to use in the carbonylation process each of the mordenites D, E and F was calcined to convert it from the ammonium form to the hydrogen form (H-form) using the calcination method described in Example 1. Each of the H-mordenites so prepared was used to catalyse the carbonylation of dimethyl carbonate as described below.

Carbonylation of Dimethyl Carbonate

A Hastelloy reactor tube was packed with 0.6 ml of a H-mordenite catalyst and 0.2 g of a gamma alumina pre-bed. The portion of the reactor tube containing the catalyst was heated by an electrical heating jacket. The reactor and heating jacket were themselves mounted in a heated cabinet to maintain the temperature of the pre-bed. The reactor was heated to 130° C. at atmospheric pressure under a flow of nitrogen gas. The gas was then changed to a mixture of 80 mole % carbon monoxide and 20 mole % hydrogen and the system was pressurised to 20 barg. The mixture was fed to the reactor from a gas header through a mass flow controller at a gas flow rate of 5000 per hour. The reactor was heated to 300° C. at a ramp rate of 3° C. per minute and held at 300° C. for two hours. Dimethyl carbonate was then fed to the reactor to provide a reactant gas mixture of 76 mole % carbon monoxide, 19 mole % hydrogen and 5 mole % dimethyl carbonate. A constant flow of reaction off-gases was taken from the high pressure side of the reactor system through a needle valve, let down to atmospheric pressure while maintaining a temperature of at least 130° C. and passed to a gas chromatograph for acetyls product analysis. The space time yield (STY) of acetyls products was calculated as the molar equivalent weight of acetic acid corresponding to the sum of the methyl acetate and acetic acid produced expressed as grams of acetic acid per hour per litre of catalyst. The results of the carbonylation reactions are given in FIG. 2.

Figure 2:
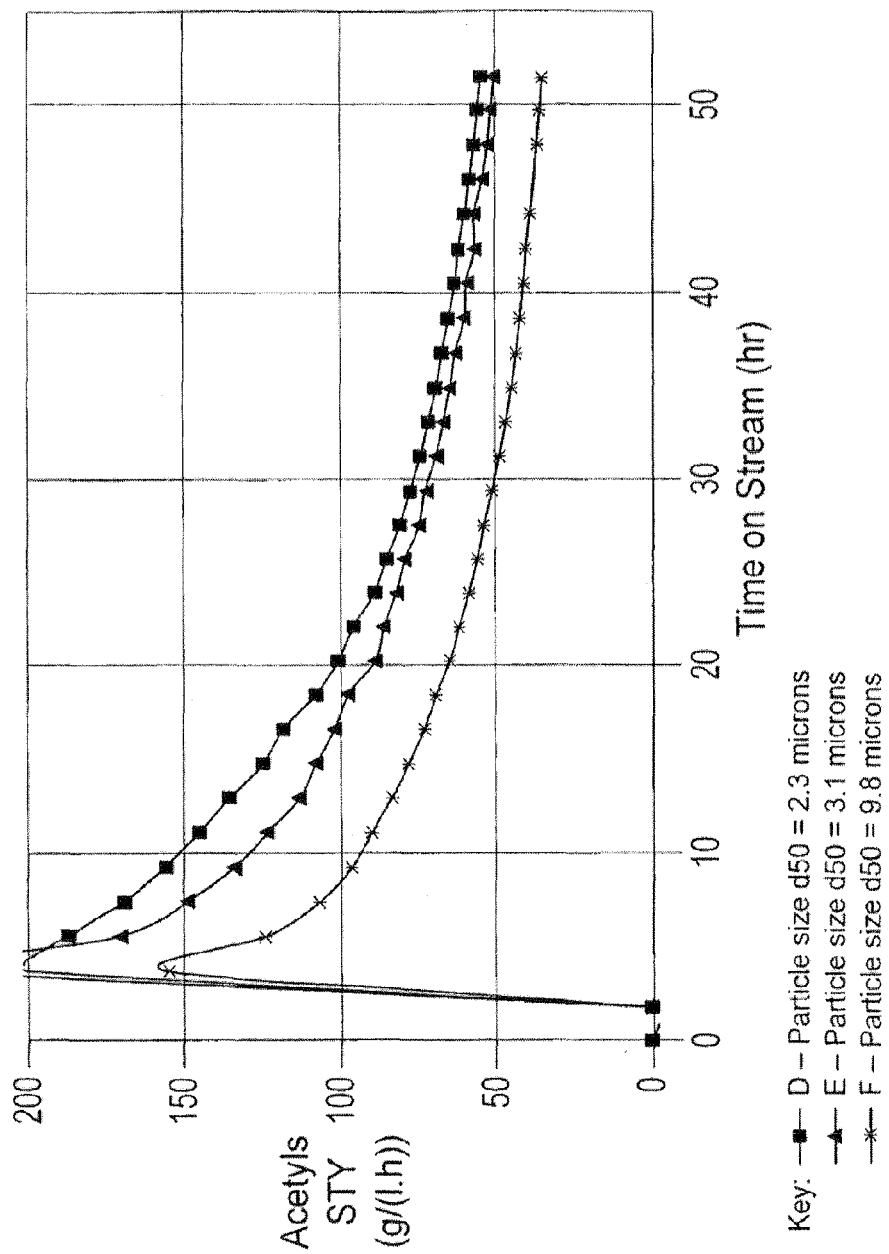
FIG. 2 depicts STY to acetyls products (g l$^{-1}$ h$^{-1}$) versus time on stream (hours) for the carbonylation of dimethyl carbonate using mordenite catalysts of similar crystal size but varying average particle sizes.

From FIG. 2 it can be seen that catalysts D and E, which have comparable mordenite crystal sizes to catalyst F but much smaller particle sizes, demonstrate superior catalytic activity compared to that achieved by catalyst F.

EXAMPLE 3

Carbonylation of Dimethyl Carbonate Using H-Mordenite Catalysts G and H

The crystal size and particle size of two commercially available mordenites in the ammonium form are given in Table 3 below.

TABLE 3

| Mordenite | Silica:alumina ratio | Crystal size (microns) | Particle size d50 (microns) |
|---|---|---|---|
| G | 20 | 0.4-0.9 | 2.3 |
| H | 20 | 0.2-0.4 | 1.0 |

The average particle size, d50 of mordenites G and H was determined using a Mastersizer 2000 laser light diffraction particle size analyser (Malvern Instruments) using the method as described in Example 1 above. The crystal size of >80% of the crystals was determined by scanning electron microscopy (SEM).

Figure 4:
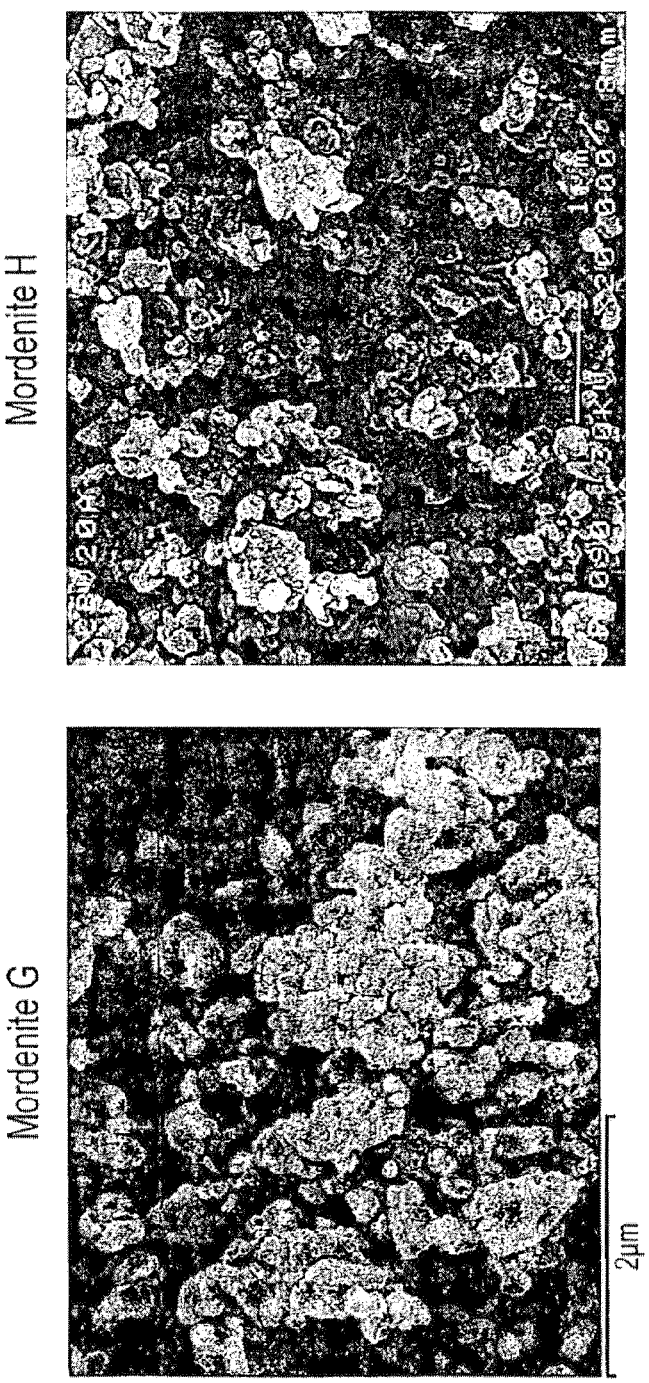
FIG. 4 depicts SEM photomicrographs of the mordenites used in Example 3.

The difference in crystal size between mordenites G and H can be gathered from the scanning electron microscope (SEM) pictures in FIG. 4. It is to be noted that the scale on the SEM for mordenite H is 1 micron and the scale on the SEM for mordenite G is 2 microns.

Calcination of Mordenites G and H

Each of mordenites G and H was calcined to convert it from the ammonium form to the H-form using the calcination method described in Example 1.

Carbonylation of Dimethyl Carbonate

Dimethyl carbonate was carbonylated using the apparatus and method described in Example 2 except that the H-form of each of mordenites G and H was used as catalyst.

Figure 3:
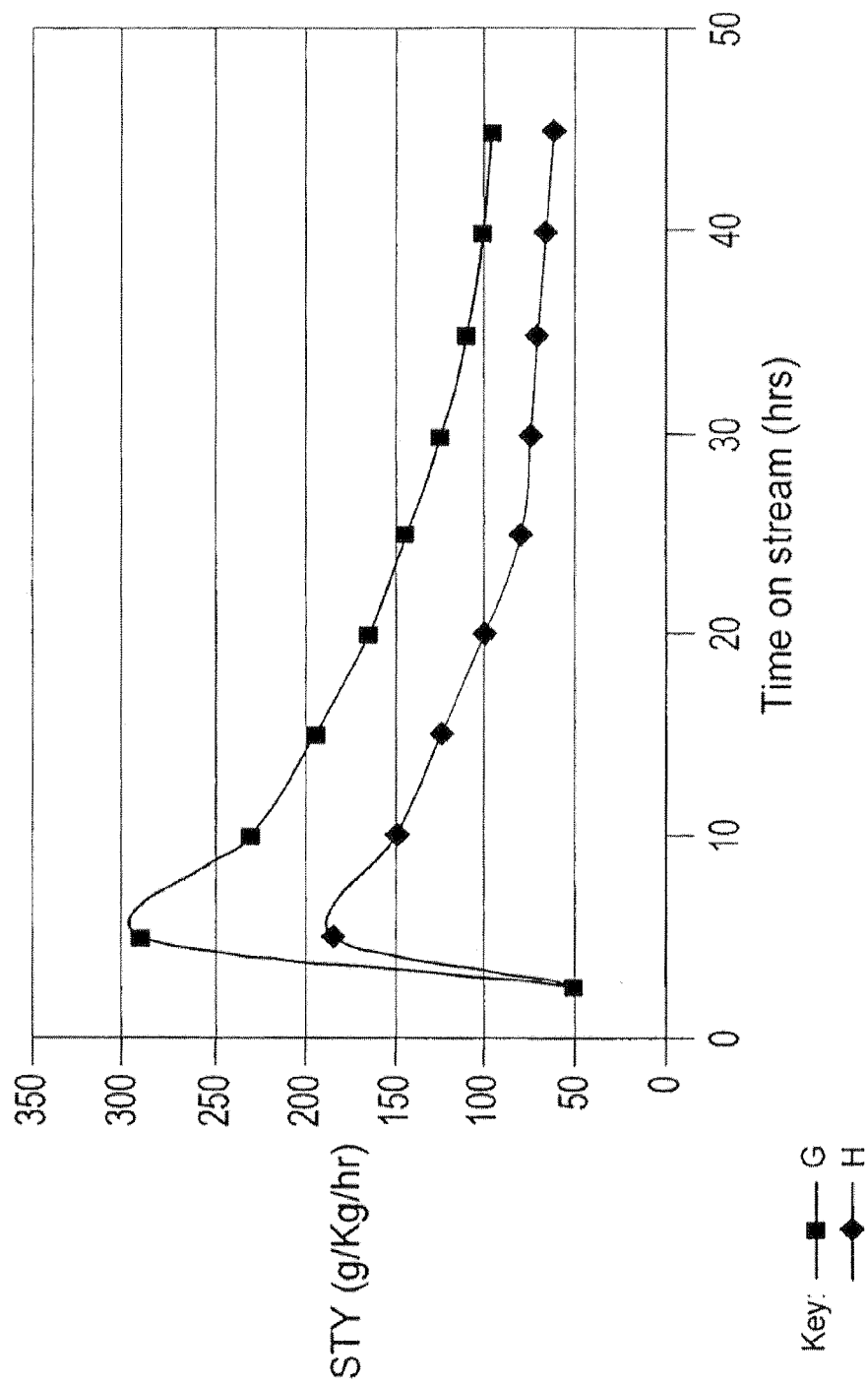
FIG. 3 depicts STY to acetyls products (g kg$^{-1}$ h$^{-1}$) versus time on stream (hours) for the carbonylation of dimethyl carbonate using mordenite catalysts of varying crystal sizes and particle sizes.

The results of the carbonylation reactions are shown in FIG. 3.

EXAMPLE 4

Preparation of Catalyst J

A mordenite zeolite with a Si/Al molar ratio of 10 was synthesized from a gel of the following molar composition:
6 Na2O:Al2O3:30 SiO2:780 H2O
by adding 1.75 g sodium aluminate to a solution of 2.32 g NaOH in 4.88 g $H_2O$. An additional 78.82 g of $H_2O$ was then added and the mixture homogenised. 12 g of Aerosil was added to the homogenised mixture and stirred for 30 minutes. The mixture was allowed to crystallise over a period of 5 days in Teflon-lined stainless steel autoclaves maintained at a temperature of 175° C. under static conditions. The formed crystals were separated by filtration, washed to pH<10 and dried at 100° C. to obtain a powder. The acid form (H-form) of the mordenite was obtained by exchanging twice with a 1.5M $NH_4NO_3$ solution at 80° C. for a period of 3 hours and then calcining at 500° C. for 2 hours. The crystal size of >80% of the crystals as determined by scanning electron microscopy (SEM) was found to be in the range 3 to 7 microns.

Carbonylation of Methanol

Catalysts I and J were used in the carbonylation of methanol with carbon monoxide. A commercially available H-mordenite having >80% of the crystals in the size range 0.1-0.5 microns and an average particle size ($d_{50}$) of 2.3 was used as Catalyst I. The H-mordenite as prepared above was used as Catalyst J.

Each carbonylation reaction was performed in a down-flow stainless steel fixed bed reactor of 10 mm internal diameter. 1 g of catalyst was loaded into the reactor after dilution with SiC (0.64 mm-0.25 mm) to obtain a bed volume of 6.4 c.c. Carbon monoxide and methanol were fed to the reactor through their respective mass-flow controllers. In order to ensure the homogeneity of the reactant mixture, methanol was vaporized and mixed with the carbon monoxide in a pre-heater maintained at 150° C. During the reaction, the pressure was controlled electronically through a Badger pneumatic valve.

Prior to the carbonylation reaction, the catalyst was activated under flowing argon (50 c.c./$g_{cat}$·h) at 350° C. (ramp of 2° C./min) for 16 hours. Carbon monoxide at a flow rate of 100 c.c./$gr_{cat}$·hr was then passed through the catalyst bed at the same temperature for 2 hours. After the activation treatment, the reaction pressure was increased to 10 bar using a flow of carbon monoxide. The carbon monoxide, argon and methanol flows were adjusted to obtain a molar ratio of $CH_3OH/CO/Ar$ of 1/10/1 and a GHSV of 3000 $h^{-1}$. The exit stream from the reactor was periodically analysed for carbonylation products and unreacted methanol and carbon monoxide by on-line gas chromatography using a Varian 3800 chromatograph equipped with three columns and two detectors. Analysis of Ar (used as reference gas), CO, $CO_2$, $H_2$, and $CH_4$ was performed using two packed columns, a Porapak Q (0.5 m length) and a 13× molecular sieve (1.5 m length), and a thermal conductivity detector (TCD). Oxygenates and C2+ hydrocarbons were analyzed using a capillary column (WCOT fused silica, 25 m length) and a flame ionization detector (FID).

The selectivity to acetyls products was calculated as (moles methyl acetate+moles acetic acid)/total moles of carbon containing products. The selectivity results for each of Catalysts I and J are shown in FIG. 5.

Figure 6:
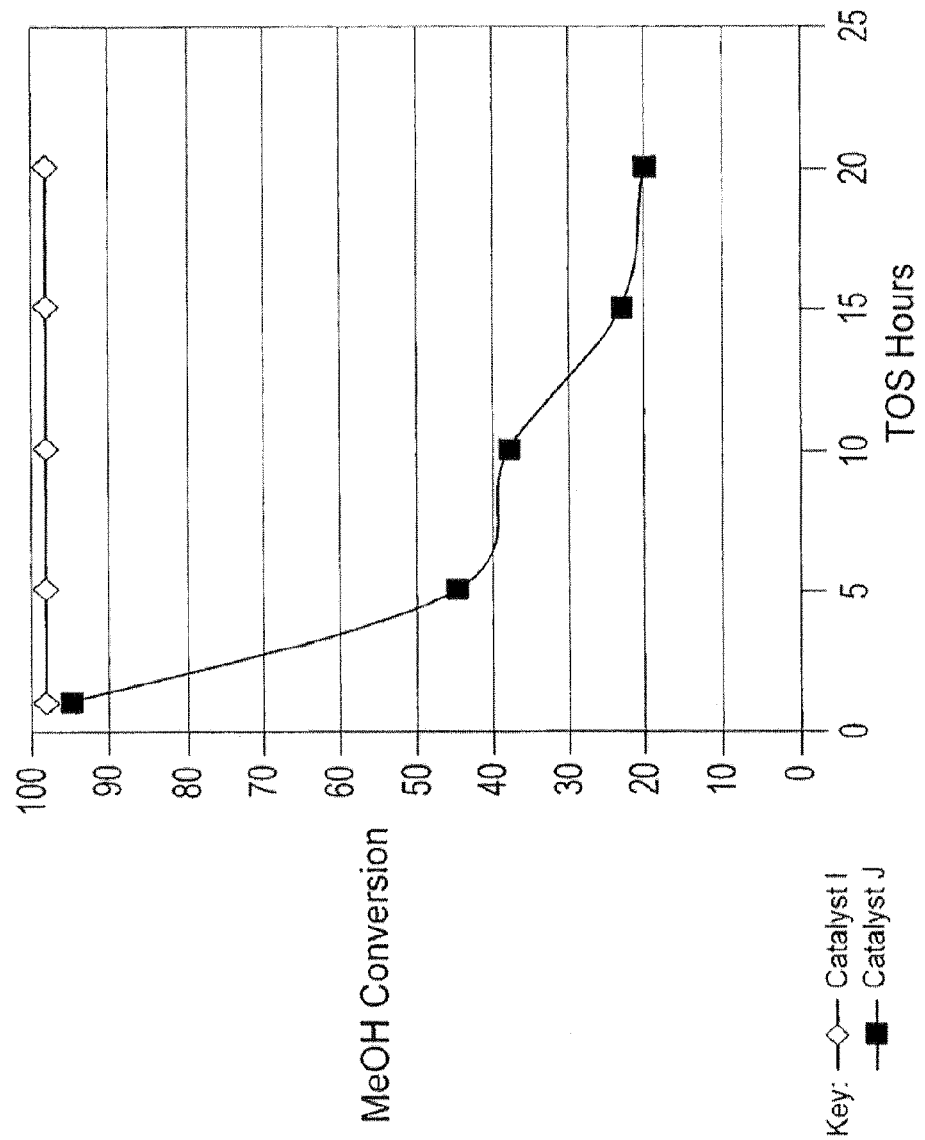
FIG. 6 depicts the degree of methanol conversion versus time on stream for the carbonylation of methanol using mordenite of different crystal sizes.

FIG. 6 shows the degree of conversion of methanol over the course of the carbonylation reaction for each of Catalysts I and J.

Figure 5:
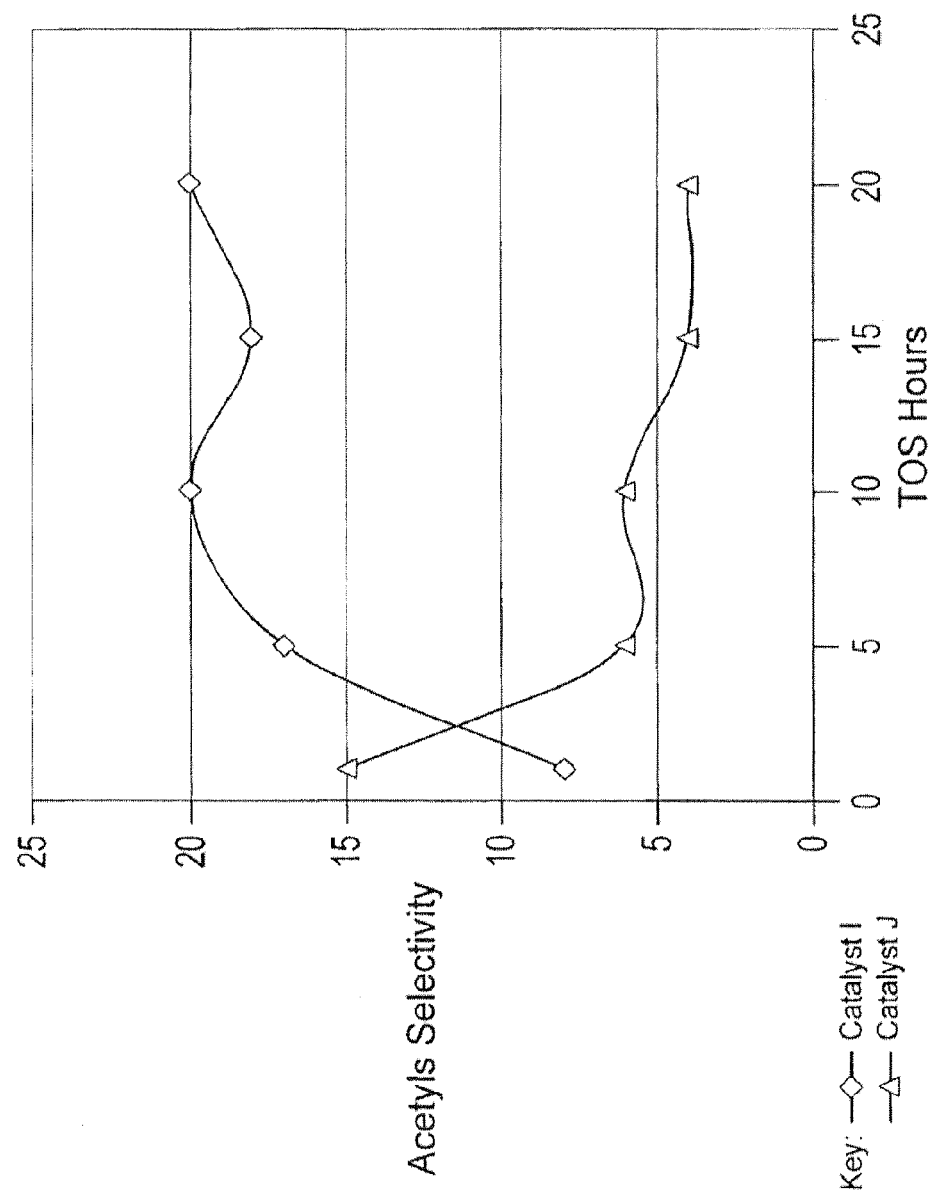
FIG. 5 depicts Selectivity to acetyls products versus time on stream for the carbonylation of methanol using mordenite of different crystal sizes.

As can be seen from FIGS. 5 and 6, Catalyst I which has a much smaller crystal size than Catalyst J provides significantly improved selectivity and activity.

The invention claimed is:

1. A process for the manufacture of at least one of acetic acid and methyl acetate comprising the step of carbonylating at least one carbonylatable reactant selected from methanol, dimethyl ether and dimethyl carbonate with carbon monoxide in the presence of a zeolite of structure type MOR, wherein the zeolite has greater than 50% of its crystals in the size range 0.1 to 3 microns.

2. A process according to claim 1 wherein greater than 50% of the crystals are in the size range 0.1 to 2 microns.

3. A process according to claim 2 wherein greater than 50% of the crystals are in the size range 0.1 to 1.5 microns.

4. A process according to claim 1 wherein greater than 80% of the crystals are in the size range 0.1 to 2 microns.

5. A process according to claim 1 wherein the zeolite has an average particle size of no greater than 6 microns.

6. A process according to claim 5 wherein the average particle size is in the range 2 to 3.5 microns.

7. A process according to claim 4 and wherein the average particle size is in the range 2 to 6 microns.

8. A process according to claim 3 and wherein the average particle size is in the range 2 to 3.5 microns.

9. A process according to claim 1 wherein the zeolite is H-mordenite.

10. A process according to claim 1 wherein the zeolite is a mordenite which has been ion-exchanged or otherwise loaded with one or more metals selected from copper, silver, gold, nickel, iridium, rhodium, platinum, palladium and cobalt.

11. A process according to claim 1 wherein the zeolite has a silica:alumina molar ratio in the range 10 to 40:1.

12. A process according to claim 1 wherein the carbonylatable reactant is dimethyl ether or dimethyl carbonate and the gaseous feed to the process contains less than 2.5 wt % water.

13. A process according to claim 1 wherein the carbonylation is conducted in the presence of hydrogen.

* * * * *